United States Patent [19]
Arnold et al.

[11] Patent Number: 5,316,935
[45] Date of Patent: May 31, 1994

[54] SUBTILISIN VARIANTS SUITABLE FOR HYDROLYSIS AND SYNTHESIS IN ORGANIC MEDIA

[75] Inventors: Frances H. Arnold; Keqin Chen, both of Pasadena, Calif.

[73] Assignee: California Institute of Technology, Pasadena, Calif.

[21] Appl. No.: 864,298

[22] Filed: Apr. 6, 1992

[51] Int. Cl.$^5$ .......................... C12N 9/50; C12N 9/56; C12N 15/57; C12P 21/00
[52] U.S. Cl. .................................. 435/222; 435/69.1; 435/68.1; 435/252.3; 435/252.33; 435/320.1; 435/219; 536/23.2; 935/10; 935/14; 935/29; 935/72; 935/74
[58] Field of Search ...................... 435/221, 222, 69.1, 435/172.3, 252.31, 320.1; 536/23.2

[56] References Cited

U.S. PATENT DOCUMENTS

| | | | |
|---|---|---|---|
| 4,760,025 | 7/1988 | Estell et al. | 435/222 |
| 4,980,288 | 12/1990 | Bryan et al. | 435/222 |
| 4,990,452 | 2/1991 | Bryan et al. | 435/222 |
| 5,116,741 | 5/1992 | Bryan et al. | 435/87 |

FOREIGN PATENT DOCUMENTS 130756 1/1985 European Pat. Off. ............ 435/222

OTHER PUBLICATIONS

Hwang, J. Y. and Arnold, F. H., 1991, in *Applied Biocatalysis*, Blanch, H. W. et al., Eds., Marcel Dekker, Inc., publisher, pp. 53–86.
Russell, A. J., et al., 1987, Journal of Molecular Biology, 193:803–813.
Martinez, P. and Arnold, F. H., 1991, Journal of the American Chemical Society, 113(16):6336–6337.
Melonn, B., et al., 1985, FEBS Letters 183(2):195–200.
Economou, C., et al., 1992, Biotechnology and Bioengineering 39(6):658–662.
Wong, C.-H., et al., 1990, Journal of the American Chemical Society, 112(3):945–953.
Roseman, M. A., 1988, Journal of Molecular Biology, 200:513–522.
Bott, R., et al., 1988, The Journal of Biological Chemistry, 263(16):7895–7906.
Richelli, F., et al., 1982, Biochemical Journal, 207:201–205.
Gorman, L. A. S., et al., 1992, Biotechnology and Bioengineering, 39(4):392–397.
Zhong, Z., et al., 1991, Journal of the American Chemical Society, 113(1):683–684.
Russell, A. J., et al., 1989, Journal of Cellular Biochemistry, 13A, p. 77, Abstract A240.
Evnin, L. B., et al., 1989, Journal of Cellular Biochemistry, 13A, Abstract A110.
Gupta, M. N., 1992, European Journal of Biochemistry, 203(1/2):25–32.
Arnold, Frances H., "Engineering enzymes for non-aqueous solvents", in Tibtech, vo.1. 8:244–249 (1990).
Chen, Keqin, et al., "Enzyme Engineering for Nonaqueous Solvents. II. Additive of Subtilisin E in Polar Organic Media", in Biotechnol. Prog., vol. 7:125–129 (1991).
Chen, Keqin and Arnold, Frances H., "Enzyme Engineering for Nonaqueous Solvents: Random Mutagenesis to Enhance Activity of Subtilisin E in Polar Organic Media", Biotechnology, vol. 9:1073–1077 (1991).
Siezen, Roland J., et al., "Homology modeling and protein engineering strategy of subtilases, the family of subtilisin-like serine proteinases", Protein Engineering, vol. 4:719–737 (1991).
Martinez, Pascal, et al., "Stabilization of Subtilisin E in Organic Solvents by Site-Directed Mutagenesis", Biotechnology and Bioengineering, vol. 39:141–147 (1992).

*Primary Examiner*—Robert A. Wax
*Assistant Examiner*—William W. Moore
*Attorney, Agent, or Firm*—Poms, Smith, Lande & Rose

[57] ABSTRACT

In accordance with the present invention, there are provided novel, modified subtilisin enzyme(s) having improved catalytic activity and/or stability in organic media.

25 Claims, 4 Drawing Sheets

SEQUENCE LISTING (1) GENERAL INFORMATION:

(iii) NUMBER OF SEQUENCES: 7

(2) INFORMATION FOR SEQ ID NO:1:

(i) SEQUENCE CHARACTERISTICS:
(A) LENGTH: 275 amino acids
(B) TYPE: amino acid
(D) TOPOLOGY: linear (ii) MOLECULE TYPE: peptide (iii) HYPOTHETICAL: NO (iv) ANTI-SENSE: NO (vi) ORIGINAL SOURCE:
(A) ORGANISM: Bacillus subtilis
(B) STRAIN: 1168

(xi) SEQUENCE DESCRIPTION: SEQ ID NO:1:

```
Ala Gln Ser Val Pro Tyr Gly Ile Ser Gln Ile Lys Ala Pro Ala Leu
 1               5                  10                  15

His Ser Gln Gly Tyr Thr Gly Ser Asn Val Lys Val Ala Val Ile Asp
            20                  25                  30

Ser Gly Ile Asp Ser Ser His Pro Asp Leu Asn Val Arg Gly Gly Ala
        35                  40                  45

Ser Phe Val Pro Ser Glu Thr Asn Pro Tyr Gln Asp Gly Ser Ser His
    50                  55                  60

Gly Thr His Val Ala Gly Thr Ile Ala Ala Leu Asn Asn Ser Ile Gly
65                  70                  75                  80

Val Leu Gly Val Ala Pro Ser Ala Ser Leu Tyr Ala Val Lys Val Leu
                85                  90                  95

Asp Ser Thr Gly Ser Gly Gln Tyr Ser Trp Ile Ile Asn Gly Ile Glu
            100                 105                 110

Trp Ala Ile Ser Asn Asn Met Asp Val Ile Asn Met Ser Leu Gly Gly
        115                 120                 125

Pro Thr Gly Ser Thr Ala Leu Lys Thr Val Val Asp Lys Ala Val Ser
    130                 135                 140

Ser Gly Ile Val Val Ala Ala Ala Gly Asn Glu Gly Ser Ser Gly
145                 150                 155                 160

Ser Thr Ser Thr Val Gly Tyr Pro Ala Lys Tyr Pro Ser Thr Ile Ala
                165                 170                 175

Val Gly Ala Val Asn Ser Ser Asn Gln Arg Ala Ser Phe Ser Ser Ala
            180                 185                 190

Gly Ser Glu Leu Asp Val Met Ala Pro Gly Val Ser Ile Gln Ser Thr
        195                 200                 205

Leu Pro Gly Gly Thr Tyr Gly Ala Tyr Asn Gly Thr Ser Met Ala Thr
    210                 215                 220

Pro His Val Ala Gly Ala Ala Ala Leu Ile Leu Ser Lys His Pro Thr
225                 230                 235                 240

Trp Thr Asn Ala Gln Val Arg Asp Arg Leu Glu Ser Thr Ala Thr Tyr
                245                 250                 255

Leu Gly Asn Ser Phe Tyr Tyr Gly Lys Gly Leu Ile Asn Val Gln Ala
            260                 265                 270

Ala Ala Gln
        275
```

( 2 ) INFORMATION FOR SEQ ID NO:2:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear     ( i i ) MOLECULE TYPE: cDNA     ( v i ) ORIGINAL SOURCE:
        ( A ) ORGANISM: PCR Primer     ( x i ) SEQUENCE DESCRIPTION: SEQ ID NO:2:

GCGGAGCAAG CTTCGTAC                                          18

( 2 ) INFORMATION FOR SEQ ID NO:3:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear     ( i i ) MOLECULE TYPE: cDNA     ( v i ) ORIGINAL SOURCE:
        ( A ) ORGANISM: PCR Primer     ( x i ) SEQUENCE DESCRIPTION: SEQ ID NO:3:

CGGGATCCTG CAGGATTCAA CATGCGGAG                      29

( 2 ) INFORMATION FOR SEQ ID NO:4:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear     ( i i ) MOLECULE TYPE: cDNA     ( v i ) ORIGINAL SOURCE:
        ( A ) ORGANISM: D248N site-directed mutagenesis primer     ( x i ) SEQUENCE DESCRIPTION: SEQ ID NO:4:

TTTCTAAACG GTTACGGACT TGC                                23

( 2 ) INFORMATION FOR SEQ ID NO:5:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear     ( i i ) MOLECULE TYPE: cDNA     ( v i ) ORIGINAL SOURCE:
        ( A ) ORGANISM: D248A site directed mutagenesis primer     ( x i ) SEQUENCE DESCRIPTION: SEQ ID NO:5:

CTAAACGAGC ACGGACT                                          17

( 2 ) INFORMATION FOR SEQ ID NO:6:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear     ( i i ) MOLECULE TYPE: cDNA (v i) ORIGINAL SOURCE:
  (A) ORGANISM: D248L site directed mutagenesis primer (x i) SEQUENCE DESCRIPTION: SEQ ID NO:6:

CTAAACGAAG ACGGACT          17

(2) INFORMATION FOR SEQ ID NO:7:

(i) SEQUENCE CHARACTERISTICS:
    (A) LENGTH: 17 base pairs
    (B) TYPE: nucleic acid
    (C) STRANDEDNESS: single
    (D) TOPOLOGY: linear (i i) MOLECULE TYPE: cDNA (v i) ORIGINAL SOURCE:
    (A) ORGANISM: N218S site directed mutagenesis primer (x i) SEQUENCE DESCRIPTION: SEQ ID NO:7:

CGCTTATAGC GGAACGT          17

SUBTILISIN VARIANTS SUITABLE FOR HYDROLYSIS AND SYNTHESIS IN ORGANIC MEDIA

ACKNOWLEDGEMENT

This invention was made with Government support under Grant No. 66766, awarded by the Department of Energy (Advanced Industrial Concepts Program) and Grant No. N0004-91-J-1397, awarded by the Office of Naval Research. The Government has certain rights in the invention.

FIELD OF INVENTION

The present invention relates to the production of proteins using recombinant techniques. More specifically, the invention relates to the generation and production of subtilisin variants using recombinant means.

BACKGROUND OF THE INVENTION

Subtilisin is a proteolytic enzyme that has considerable utility in food processing and laundry applications for degrading proteinaceous materials. In addition to these applications, subtilisin is also capable of promoting a wide variety of chemical conversions, such as peptide synthesis; the resolution of racemic alcohols, esters and amines; the regioselective acylation of polyhydroxy-compounds such as glycols, steroids and sugars, and the like. Many of these chemical reactions must be carried out in organic media in order to be practically useful. While useful to some extent for conducting such reactions in organic media, subtilisins exhibit relatively low levels of enzymatic activity in organic media. This relative lack of activity in organic solvents severely limits the commercial and industrial applications of subtilisin enzymes in chemical synthesis. In view of this, it would be desirable to be able to produce modified subtilisins which have improved activities in organic media.

Subtilisin has found considerable utility in industrial and commercial applications [see, for example, U.S. Pat. No. 3,623,957 and J. Millet, J. Appl. Bact. 33:207 (1970)]. For example, subtilisins and other proteases are commonly used in detergents for the removal of protein-based stains. They also are used in food processing to accommodate the proteinaceous substances present in the food preparations to their desired impact on the composition.

Subtilisins have also been employed in organic synthesis to catalyze a wide variety of chemical reactions in organic media. For example, the resolution of racemic alcohols employing hydrolases is reviewed by Klibanov in Accts. Chem. Res. Vol. 23:114 (1990). The use of subtilisin for the resolution of racemic amines in anhydrous organic solvent is described by Kitaguchi et al., in J. Am. Chem. Soc. Vol. 111:3094 (1989).

Regioselective acylation of 5α-androstane-3β, 17β-diol, promoted by subtilisin in anhydrous acetone, has been described by Riva and Klibanov in J. Am. Chem. Soc. Vol. 110:3291 (1988). Similarly, subtilisin has been used for the regioselective acylation of the primary hydroxyls of unprotected mono- and oligosaccharides in anhydrous dimethylformamide and pyridine [see Riva et al, J. Am. Chem. Soc. Vol. 110:584 (1988)].

Subtilisin has also been used for the synthesis of peptides in organic solvents [see, for example, Ferjancic et al., Appl. Microbiol. Technol. Vol. 32:65 (1990)]. In addition to solubilizing the reactants, organic solvent alters the relative amidase and esterase activities of the enzyme, providing a catalyst that is well-suited to peptide synthesis by aminolysis [see, for example, Wong and Wang, Experientia 47:1123 (1991)]. The ability of enzymes such as subtilisin to discriminate between optical isomers of a substrate can also be altered by carrying out such reactions in organic solvents. For example, D-amino acid-containing peptides can be prepared using subtilisin in anhydrous tert-amyl alcohol [see Margolin et al., J. Am. Chem. Soc. Vol. 109:7885 (1987)].

Enzymes having characteristics which vary from available stock are required. In particular, enzymes having enhanced catalytic activity and/or stability in non-aqueous media will be useful in extending the range of processes for which such enzymes can be employed. Other characteristics which one may wish to vary relative to available stock include enzyme shelf life and an enzyme's ability to withstand exposure to high temperatures. Because many industrial processes are conducted at temperatures that are above the stability range of many enzymes, highly stable proteases not only will be advantageous to certain industries such as detergent and hide dehairing, that already require stable proteases, but may be useful in industries that currently use chemical means to carry out the reactions described earlier: peptide synthesis, resolution of racemic compounds, acylation reactions, and the like.

Chemical modification of enzymes is known. Such modifications have been carried out primarily to improve the stability of the target enzyme. For example, see Svendsen, I., Carlsberg Res. Commun. 41(5): 237-291 (1976). The ability of chemical modification to impart improved catalytic activity (rather than stability), however, has not been reported. While chemical modification of active-site residues of the serine protease chymotrypsin results in dramatic change in the ratio of esterase-to-amidase activities (Wong and Wang, supra), the modifications drastically reduce the reaction rates.

Chemical modification methods, moreover, suffer from numerous disadvantages, e.g., being dependent upon the presence of amino acid residues convenient for such modification. In addition, these methods are frequently nonspecific in that all accessible residues with common side chains are modified, and such methods are not capable of reaching sterically and/or electronically inaccessible amino acid residues without further processing (e.g., denaturation; once denatured, it is generally not possible to fully reinstitute enzyme activity). To the extent that such methods have the objective of replacing one amino acid residue side chain for another side chain or equivalent functionality, then mutagenesis promises to supplant such methods.

Substantial work has been done to develop variants of subtilisin which exhibit useful new properties, including increased thermostability [Pantoliano et al., Biochemistry Vol. 28:7205 (1989); Pantoliano et al., Biochemistry Vol. 26:2077 (1987); Takagi et al., J. Biol. Chem. Vol. 265:6874 (1990)], to increase the ratio of esterase to amidase activity for peptide synthesis [Abrahmsen et al., Biochemistry Vol. 30:4151 (1991)], to alter the pH dependence of the catalytic activity [Thomas et al., Nature Vol. 318:375 (1985); Wells and Estell, TIBS Vol. 13:291 (1988)], to increase resistance to chemical oxidation [Estell et al., J. Biol. Chem. Vol. 260:6518 (1985)], to increase amidase activity [Takagi et al., J. Biol. Chem. Vol. 263:19592 (1988)], and to alter substrate specificity [Wells et al., Proc. Natl. Acad. Sci. USA Vol. 84:5167 (1987); Carter and Wells, Science Vol. 237:394 (1987)].

Modifying the activity/stability/pH-activity profiles of subtilisins (especially in organic media) would be desirable in making these enzymes more widely applicable in a wide variety of processes. For example, enhancing the enzymatic activity of subtilisins in organic media will make it possible to use such enzymes in reactions which are preferably conducted in organic media, such as, for example, peptide synthesis, and the like.

Mutations of proteases such as subtilisins will hopefully provide a variety of different proteases having modified properties such as improved $K_m$, $k_{cat}$, $K_m/k_{cat}$ ratio and substrate specificity. These mutations would then allow such enzymes to be tailored for the particular medium to be employed, or the substrate which is anticipated to be present, for example in peptide synthesis, or for hydrolytic processes such as laundry uses.

BRIEF DESCRIPTION OF THE INVENTION

In accordance with the present invention, we have developed modified subtilisin enzyme(s) having improved catalytic activity and/or stability in organic media.

Invention enzymes are useful for the catalysis of a variety of reactions which are preferably carried out in organic media, such as transesterification, peptide polymer synthesis, selective acylation reactions, and the like.

DETAILED DESCRIPTION OF THE INVENTION

In accordance with the present invention, there are provided "subtilisin enzymes" having improved catalytic activity and/or stability in organic media, relative to the catalytic activity and/or stability of subtilisin enzymes in organic media, said modified enzymes characterized by having at least one of residues 60, 97, 103, 131, 181, 182, 188, 248 or 255, and optionally 156 and/or 218, replaced with a residue which does not naturally occur at the corresponding position, wherein the position of each residue is given relative to subtilisin type BPN'.

Mature Bacillus subtilisin molecules are composed of a single polypeptide chain of different lengths, depending on the source from which the subtilisin is obtained. For example, for subtilisin type Carlsberg produced by *Bacillus licheniformis* [Smith et al., J. Biol. Chem., 243:2184–2191 (1968)]; and the subtilisin produced by *Bacillus subtilis* (strain DY; [Nedkov et al., Hoppe-Seyler's Z, Physiol. Chem. Vol. 364:1537–1540 (1983)] each contain 274 residues; or subtilisin type BPN' produced by *Bacillus amyloliquefaciens* [Markland et al., J. Biol. Chem. 242: 5198-5211 (1967)]; the aprA gene product of *Bacillus subtilis* [also known as subtilisin I168 or subtilisin E, see Stahl et al., J. Bacteriol., 158:411–418 (1984)]; and the subtilisin of *Bacillus mesentericus* [Svendsen et al., FEBS Letters 196: 220–232 (1986)], each contain 275 residues; while subtilisins obtained from other sources have longer or shorter sequences.

When comparing amino acid sequences of subtilisin from different strains of Bacillus herein, the sequence of subtilisin BPN' is used as a standard. For example, based on an alignment of sequences that gives the highest degree of homology between subtilisin Carlsberg and subtilisin BPN', the serine at the active site of the former is referred to a serine 221, even though it is located at position 220 of the amino acid sequence. On the same basis, position 220 of the amino acid sequence of subtilisin Carlsberg may be said to "correspond" to position 221 of subtilisin BPN'. See e.g., Nedkov et al., supra.

In the family of Bacillus subtilisins, complete amino acid sequences are presently available for at least fourteen subtilisins [see Siezen et al., in Protein Engineering 4:719-737 (1991)]. Subtilisin Carlsberg and subtilisin BPN' (sometimes referred to as subtilisin Novo) differ by 84 amino acids and one additional residue in BPN' (subtilisin Carlsberg lacks an amino acid residue corresponding to residue 56 of subtilisin BPN'). Subtilisin DY comprises 274 amino acids and differs from subtilisin Carlsberg in 32 amino acid positions and from subtilisin BPN' by 82 amino acid replacements and one deletion (subtilisin DY lacks an amino acid residue corresponding to residue 56 of subtilisin BPN'). The amino acid sequence of the aprA gene product is 85% homologous to the amino acid sequence of subtilisin BPN'. Thus, there is extensive homology between amino acid sequences of subtilisins from different strains of Bacillus. There is also strong homology between the amino acid sequences of subtilisin-like enzymes from different organisms (see Siezen et al., supra). This homology is particularly strong in certain regions of the molecule and especially in those that play a role in the catalytic mechanism and in substrate binding. Examples of such conserved sequences are the primary and secondary substrate binding sites, $Ser^{125}$-$Leu^{126}$-$Gly^{127}$-$Gly^{128}$ and $Tyr^{104}$ respectively and the sequence around the reactive serine (221), $ASN^{218}$-$Gly^{219}$-$Thr^{220}$-$Ser^{221}$-$Met^{222}$-$Ala^{223}$. Conserved regions of the subtilisin sequences are indicated in Siezen et al., supra.

Subtilisins contemplated for use in the practice of the present invention are preferably Class I subtilisin enzymes, as defined by Siezen et al., supra. Exemplary Class I subtilisin enzymes include subtilisin BPN' (BASBPN), subtilisin I168 (aprA or BSS168), subtilisin DY (BSSDY), subtilisin Carlsberg (BLSCAR), subtilisin PB92 (BAPB92), alkaline elastase YaB (BYSYAB), subtilisin 147 (BLS147), minor extracellular protease (BSEPR), intracellular serine protease 1 (BSISP1), thermitase (TVTHER), basic protease (DNEBPR), extracellular protease, obtained from Xanthomonas campestris (XCEXPR), bacillopeptidase F (BSBPF), cytolysin component A (EFCYLA), epidermin leader protease (SEEPIP), C5a peptidase (SPSCPA), SK11 cell wall proteinase (LLSK11), extracellular serine protease, obtained from Serratia marcescens IF03046 (SMEXSP), Ca-dependent protease (AVPRCA), pituitary PC3 protease (MMPPC3), insulinoma PC2 protease (HSIPC2), furin (HSFURI), furin 1 (DMFUR1), Kex1 serine protease (KLKEX1), Kex2 serine protease (SCKEX2), alkaline protease, obtained from Bacillus sp. DSM 4828 (BDSM48), intracellular serine protease, obtained from Bacillus subtilis A50 (BSIA50), extracellular serine protease, obtained from Bacillus thuringiensis (BTFINI), extracellular serine protease, obtained from Bacillus cereus (BCESPR), and the like.

Presently preferred subtilisins for use in the practice of the present invention include subtilisin BPN' (BASBPN), subtilisin I168 (aprA or BSSI68), subtilisin DY (BSSDY), subtilisin Carlsberg (BLSCAR), subtilisin PB92 (BAPB92), alkaline elastase YaB (BYSYAB), subtilisin 147 (BLS147), minor extracellular protease (BSEPR), intracellular serine protease 1 (BSISP1), and thermitase (TVTHER).

Presently preferred amino acid substitutions are those that enhance the activity and/or stability of subtilisins in organic solvents. Substitutions which are effective for this purpose include the following, which are reported starting from the amino acid sequence of subtilisin E (subtilisin I168):

| Amino acid position | Substitution | Abbreviation |
|---|---|---|
| 60 | Asp → Asn | D60N |
| 97 | Asp → Gly | D97G |
| 103 | Gln → Arg | Q103R |
| 131 | Gly → Asp | G131D |
| 156 | Glu → Gly | E156G |
| 181 | Asn → Ser | N181S |
| 182 | Ser → Gly | S182G |
| 188 | Ser → Pro | S188P |
| 218 | Asn → Ser | N218S |
| 248 | Asp → Asn | D248N |
| 248 | Asp → Ala | D248A |
| 248 | Asp → Leu | D248L |
| 255 | Thr → Ala | T255A | as well as combinations of any two or more thereof.

Amino acids are referred to throughout this specification with reference to their usual, three- and one-letter abbreviations routinely used in the art, i.e.:

| Amino Acid | Abbreviation | |
|---|---|---|
| L-Alanine | Ala | A |
| L-Arginine | Arg | R |
| L-Asparagine | Asn | N |
| L-Aspartic acid | Asp | D |
| L-Cysteine | Cys | C |
| L-Glutamine | Gln | Q |
| L-Glutamic Acid | Glu | E |
| L-Glycine | Gly | G |
| L-Histidine | His | H |
| L-Isoleucine | Ile | I |
| L-Leucine | Leu | L |
| L-Lysine | Lys | K |
| L-Methionine | Met | M |
| L-Phenylalanine | Phe | F |
| L-Proline | Pro | P |
| L-Serine | Ser | S |
| L-Threonine | Thr | T |
| L-Tryptophan | Trp | W |
| L-Tyrosine | Tyr | Y |
| L-Valine | Val | V |

Nearly all of the above-recited amino acid substitutions, which have been found to enhance subtilisin (e.g., subtilisin I168) activity in organic media, are individually found in subtilisins from other sources. Thus, the specific residue identified herein for incorporation into a modified subtilisin derivative refers to a subtilisin which does not naturally contain that residue. Naturally occurring subtilisins which have the individual substitutions identified herein include:

| Amino acid Substitution | Subtilisins containing the specified amino acid residue |
|---|---|
| D60N | TVTHER, AVPRVA, HSFURI |
| D97G | BASBPN, BAPB92, BYSYAB, BSISP1, DNEBPR, XCEXPR, SEEPIP |
| Q103R | None |
| G131D | BSEPR, BSISPI, SMEXSP, MMPPC3, HSFURI, KLKEXI, DMFURI, SCKEX2 |
| E156G | AVPRCA, MMPPC3, HSIPC2, HSFURI, DMFUR1, KLKEX1, SCKEX2 |
| N181S | BSISP1, SPSCPA, SMEXSP, MMPPC3. |
| S182G | None |
| S188P | DNEBPR, KLKEX1, SCKEX2 |
| N218S | BLS147, BSEPR, TVTHER, SEEPIP, SPSCPA, LLSK11, SMEXSP, HSIPC2 |
| T255A | None |

In addition, due to the additive benefits of the subtilisin modifications described herein, a multiplicity of the above-described modifications can be incorporated into a subtilisin derivative to improve the activity thereof.

As employed herein, the phrase "catalytic activity", when used in reference to subtilisin enzymes, means an increase in the $k_{cat}$ or a decrease in the $K_M$ for a given substrate, reflected in an increase in the $k_{cat}/K_M$ ratio. Catalytic activity can be conveniently measured by determining the ability of subtilisin to hydrolyze a substrate such as succinyl-Ala-Ala-Pro-Phe-p-nitroanilide or succinyl-Ala-Ala-Pro-Met-p-nitroanilide to produce para-nitroaniline.

A change in substrate specificity is defined as a difference between the $k_{cat}/K_m$ ratio of the precursor enzyme and that of the mutant. The $k_{cat}/K_m$ ratio is a measure of catalytic efficiency. Subtilisins with increased or diminished $k_{cat}/K_m$ ratios are described in the examples. Generally, the objective will be to secure a mutant having a greater (numerically larger) $k_{cat}/K_m$ ratio for a given substrate, thereby enabling the use of the enzyme to more efficiently act on such target substrate. An increase in $k_{cat}/K_m$ ratio for one substrate may be accompanied by a reduction in $k_{cat}/K_m$ for another substrate. This is a shift in substrate specificity, and mutants exhibiting such shifts have utility where the precursors are undesirable, e.g. to prevent undesired hydrolysis of a particular substrate in an admixture of substrates.

$k_{cat}$ and $K_m$ are measured in accord with known procedures, or as described in Example X.

As employed herein, the term "stability", when used in reference to the stability of subtilisin enzymes, means the half-life of said enzyme when exposed to elevated temperature and/or organic media. In general, the higher the temperature to which the enzyme is exposed, the shorter the half-life of said enzyme (i.e., the shorter the enzyme retains its activity). Similarly, the greater levels of organic solvent to which said enzymes are exposed, the shorter the half-life of said enzyme. Some of the invention subtilisins are found to have substantially higher half-lives than are the precursor enzymes from which they are derived.

As employed herein, the phrase "organic media", refers to solvent systems containing polar organic compounds such as dimethylformamide (DMF), dimethyl acetamide acetonitrile, ethanol, methanol, butanol, acetone, tetrahydrofuran, dioxane, and the like; non-polar organic compounds such as hexane, benzene, toluene, and the like; as well as mixtures of any two or more thereof, and aqueous solutions containing same.

In accordance with additional embodiments of the present invention, there are contemplated DNA sequence(s) encoding the above-described modified enzyme(s), expression vector(s) containing such DNA, and host cells containing such DNA sequence(s) and/or expression vector(s) as described above. In addition, there is also provided a process for the production of the above-described modified enzyme, said process comprising expressing DNA encoding said modified enzyme in a suitable host.

In accordance with still another embodiment of the present invention, there is provided a method for identifying amino acid substitutions which render a subtilisin derivative more active and/or more stable in organic media than is the parental subtilisin from which said derivative is derived, said method comprising:

effecting a mutation of wild-type subtilisin or a derivative thereof, and testing for an increase in activity and/or stability in organic media resulting from said mutation.

Those of skill in the art recognize that mutagenesis of subtilisin can be carried out in a variety of ways. A presently preferred way to conduct such mutagenesis is described in greater detail in Example II, employing a modified polymerase chain reaction (PCR) protocol. By using PCR primers which each fall within, or near, the targeted coding region for subtilisin, and then carrying out multiple cycles of PCR in medium containing a small amount of dimethyl sulfoxide (DMSO) and limiting quantities of dATP, genes encoding variants of subtilisin are generated at moderate frequency.

Alternatively, random mutagenesis of the subtilisin gene can be carried out using chemical mutagens, as described by Bryan et al., Proteins: Struct. Funct. Genet. 1:326 (1986). Another alternative for the mutagenesis is site-directed mutagenesis, which can be employed to introduce specific modifications into the subtilisin sequence at specified positions. Site-directed mutagenesis can be used to randomly incorporate DNA mutations at a specific position in the corresponding amino acid sequence, as described by Martinez and Arnold, J. Am. Chem. Soc. Vol. 113:6336 (1991). Sets of subtilisin genes containing various mutations are produced by these techniques.

The mutated genes are then incorporated into an expression vector which is used to transform suitable host cells. The variant enzymes are expressed by the host cells, which are screened in order to identify those that express an enzyme variant exhibiting desired characteristics, e.g. enhanced activity, stability, or altered substrate specificity in organic solvent.

The screening process of this invention consists of a rapid (preferably visual) assay for subtilisin activity in the presence of a polar organic solvent. Active enzyme forms a visible halo surrounding the bacterial colony on agar plates containing the broad subtilisin substrate casein. Halo formation on casein plates has been used previously to screen for thermostable subtilisin variants (Bryan et al., supra). In the current procedure, those enzyme variants that exhibit enhanced activity in organic solvents are found by screening on casein plates that contain a polar organic solvent, as described in Example IV. However, it is not possible to use high concentrations of polar solvents in these plates because 1) the activities of wild-type subtilisin and derivatives are too low to be visible in higher concentrations of the solvent and 2) the casein appears to dissolve more readily in some of these solvents, also making the halos indistinguishable. Therefore relatively low concentrations of organic solvent, such as dimethylformamide (DMF), are used (27–35% DMF) for the screening. This, however, does not pose a serious problem. It is demonstrated herein that the enzyme variants found using this screening method exhibit enhanced activities in the presence of very high concentrations of solvent as well (Example XII and XX). It is also demonstrated herein that it is critical to use the organic solvent in the screening process (see Example XV). It has also been demonstrated that useful mutations identified in the presence of one polar solvent, dimethylformamide, are also effective in enhancing activity in the presence of other organic solvents (see Example XX).

Once colonies with larger halos have been identified, the enzymes can be purified from these cells and subjected to further characterization. In fact, additional screening on different substrates (e.g. specific amide or ester substrates) can be performed. In accordance with the present invention, it has been found that the particular substrate used in any subsequent screening step is reflected in the properties of the resulting enzyme variant. For example, mutations that affect substrate specificity and $K_M$ in organic solvents can be found when a second screening is performed using a specific peptide substrate, succinyl-Ala-Ala-Pro-Phe-p-nitroanilide, as described in Example XIV.

If mutations that enhance enzyme stability in organic solvents are desired, then the screening is carried out in a slightly different way. Mutants with higher catalytic activity than wild-type will quickly cause larger halos to form on the casein plates. On the other hand, screening for enhanced stability is carried out after incubating the enzymes for a given period of time in the presence of the organic solvent (or at high temperatures) (see Example V). In this process, one selects those enzymes that remain active after the wild-type no longer is able to produce a halo.

Organic solvents, both polar and nonpolar, dramatically reduce the catalytic efficiency of subtilisins and other enzymes. In addition to reducing $k_{cat}$, the catalytic constant, organic solvents have a major effect on the Michaelis constant $K_M$, which reflects substrate binding to the enzyme binding pocket. Because the increases in $K_M$ are so large in polar organic solvents, mutations that reduce $K_M$ (an increased affinity for the substrate) are useful. In addition, mutations that increase $k_{cat}$ are useful. Generally, the objective is to identify mutants that increase the ratio $k_{cat}/K_M$, known as the enzyme's catalytic efficiency for the target substrate, in organic solvents, thereby enabling the use of the enzyme to more efficiently act upon such target substrate. Such mutations are described in the examples.

The enzymes herein may be obtained as salts. It is clear that the ionization state of a protein will be dependent on the pH of the surrounding medium, if it is in solution, or of the solution from which it is prepared, if it is in solid form. Acidic proteins are commonly prepared as, for example, the ammonium, sodium, or potassium salts; basic proteins as the chlorides, sulfates, or phosphates. Accordingly, the present application includes both electrically neutral and salt forms of the designated subtilisin, and the term subtilisin refers to the organic structural backbone regardless of ionization state.

The mutants described herein can be used in organic synthetic applications such as peptide synthesis, resolution of chiral racemic mixtures, regioselective acylation, and the like. In accordance with a further embodiment of the present invention, there is provided an improved process for subtilisin-promoted polymerization of amino acid esters in organic media, said method comprising carrying out said reaction with modified enzyme as described herein, under suitable reaction conditions (see Example XXI). The modified subtilisins described herein are capable of carrying out peptide synthesis in higher concentrations of organic solvent, where the features of the resulting peptide product can be dramatically altered. The modified subtilisins also exhibit higher activities than wild-type enzyme in the organic solvent.

In accordance with a further embodiment of the present invention, there is provided an improved process for subtilisin-promoted transesterification in organic media, said method comprising carrying out said reaction with modified enzyme as described herein, under suitable reaction conditions (see, for example, Example XX). The modified subtilisins exhibit higher activities than wild-type enzyme in the organic solvent.

Other subtilisin-promoted reactions contemplated by the present invention include synthesis of specific peptides, regioselective acylation of carbohydrates and other polyhydroxy-compounds, resolution of racemic esters, alcohols, and amines, and the like.

In accordance with the present invention, subtilisin-promoted reactions are preferably carried out in polar or non-polar organic reaction media as described above, as well as aqueous media containing same.

The mutants described herein can also be used in the food processing and cleaning arts. The carbonyl hydrolases, including mutants, are produced by fermentation as described herein and recovered by suitable techniques. See for example K. Anstrup, Industrial Aspects of Biochemistry, ed. B. Spencer pp. 23–46 (1974). They are formulated with detergents or other surfactants in accord with methods known per se for use in industrial processes, especially laundry. In the latter case the enzymes are combined with detergents, builders, bleach and/or fluorescent whitening agents as is known in the art for proteolytic enzymes. Suitable detergents include linear alkyl benzene sulfonates, alkyl ethoxylated sulfate, sulfated linear alcohol or ethoxylated linear alcohol. The compositions may be formulated in granular or liquid form. See for example U.S. Pat. Nos. 3,623,957; 4,404,128; 4,381,247; 4,404,115; 4,318,818; 4,261,868; 4,242,219; 4,142,999; 4,111,855; 4,011,169; 4,090,973; 3,985,686; 3,790,482; 3,749,671; 3,560,392; 3,558,498; and 3,557,002.

The invention will now be described in greater detail by reference to the following non-limiting examples.

EXAMPLES

EXAMPLE I

Construction of the *B. subtilis* expression vector pKWC

Figure 1:
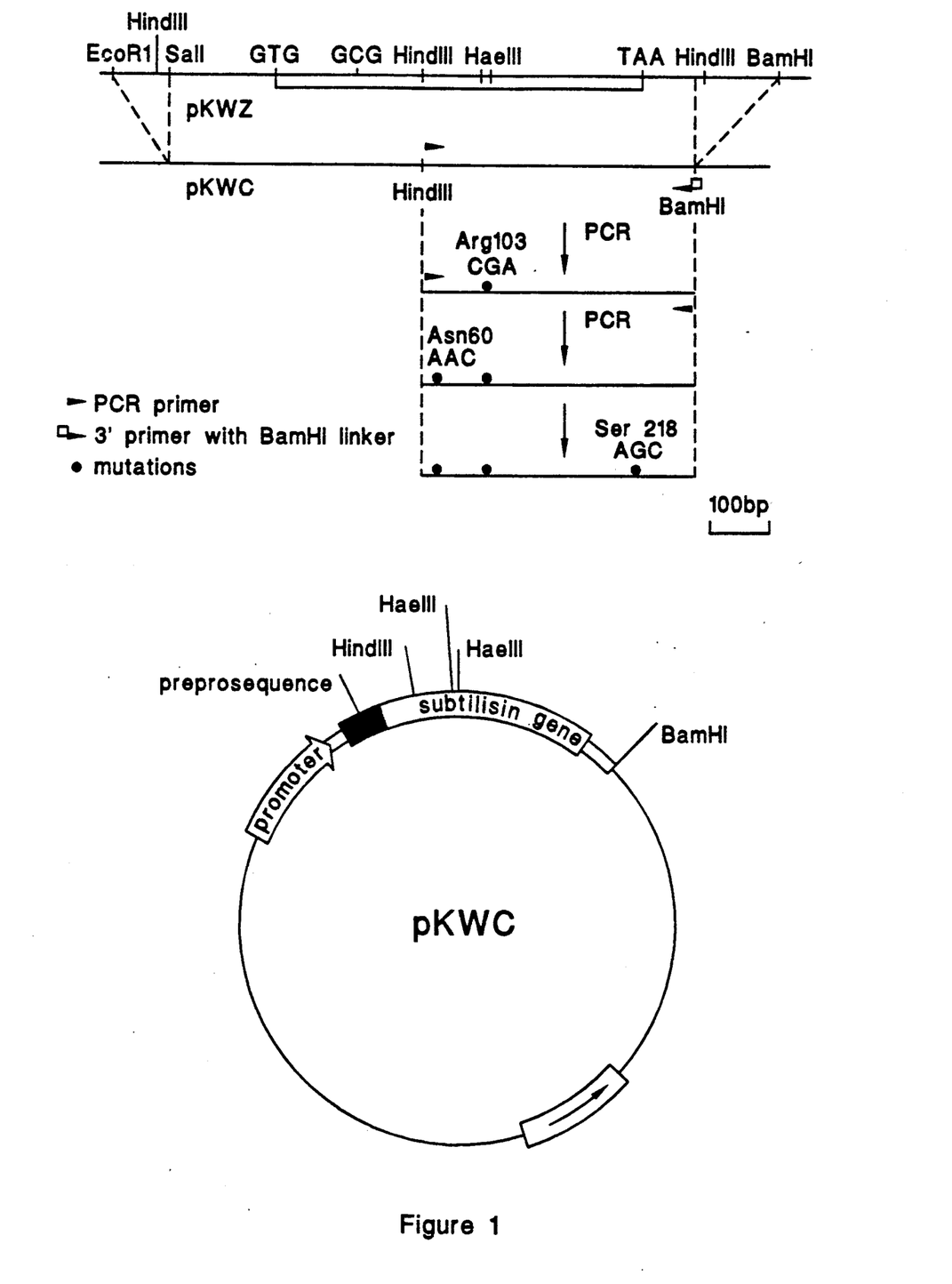
FIG. 1 shows the scheme used for construction of plasmid pKWC and random mutagenesis of subtilisin E, whose coding region is framed in pKWZ. In addition, the figure includes a partial restriction map of plasmid pKWC.

The subtilisin E expression vector pKWC was constructed by removing two HindIII sites, and one BamHI site, from plasmid pKWZ [kindly provided by R. Doi, UC Davis; see Park et al., J. Bacteriol. Vol. 171:2657-2665 (1989)] The DNA fragment containing the HindIII site from the upstream region of the subtilisin promoter of vector pKWZ was removed by double digestion with EcoRI and SalI. The sticky ends of the plasmid were filled using Klenow fragment and ligated using T4 DNA ligase. A BamHI linker attached to the PCR 3' primer was used to delete a PstI-BamHI fragment downstream of the subtilisin gene, which contained another HindIII site. A restriction map of the resulting vector, pKWC, is shown in FIG. 1. The sequence of the subtilisin E gene has been published [see Stahl and Ferrari in J. Bacteriol. 158:411–418 (1984)], and is reproduced herein as SEQ ID NO: 1.

EXAMPLE II

Random mutagenesis of the subtilisin gene using polymerase chain reaction (PCR)

The HindIII-BamHI DNA fragment which encodes mature subtilisin E from amino acid residue 49 to the C-terminus was chosen as the target for random murtagenesis (see FIG. 1). Two oligonucleotides, SEQ ID NO; 2 and SEQ ID NO: 3, were used as 5' and 3' PCR primers, respectively:

SEQ ID NO: 2:
5'-GCGGAGCAAGCTTCGTAC-3'  and

SEQ ID NO: 3:
5'-CGGGATCCTGCAGGATTCAACATGCGGAG-3'.

Two restriction sites, PstI and Bam HI, were added to the 3' primer for convenience in the subsequent cloning steps. The PCR was carried out essentially as previously described [see Saiki eta al., Science 239:487–491 (1988); and Leung et al., Teucnique 1:11-15 (1989)] on 50 ng of single-stranded target DNA. A 100 μl reaction mixture contained 10 mM Tris-HCl, pH 8.0, 20 mM KCl, 1.5 mM MgCl$_2$, 0.01% (w/v) gelatin, 10 mM β-mercaptoethanol, 10 μl DMSO, 1 mM each of dGTP, dCTP and dTTP, 0.2 mM dATP, 1.5 μl each of the 5' and 3' primers (0.4 mg/ml), and 0.5 μl AmpliTaq TM DNA polymerase (5U/μl) (Perkin Elmer-Cetus). PCR was carried out at 94° C. for 1 minute, 42° C. for 2 minutes, and 72° C. for 3 minutes. The last chain extension reaction was carried out at 72° C. for 7 minutes, and a total of 25 cycles were performed. The size and yield of the amplified DNA fragments were determined by agarose gel electrophoresis.

EXAMPLE III

Preparations of mutant DNA libraries of subtilisin

To construct a randomly mutated mini-DNA library, plasmid pKWC (prepared as described in Example I) and the PCR-generated subtilisin DNA fragments (prepared as described in Example II) were digested with HindIII and BamHI. Appropriate vector and insert fragments were separated by agarose gel electrophroesis, purified from the agarose gel and ligated. These constructs were transformed into a subtilisin-deficient *B. subtilis* strain, DB 428 [kindly provided by R. Doi, UC Davis]; using the procedure of Dubnau et al. [see Dubnau and Davidoff-Abelson, J. Mol. Biol. 56:209-221 (1971); and Gryczan et al., Bacteriol. 134:318-329 (1978)].

EXAMPLE IV

Screening transformed *B. subtilis* for enhanced subtilisin E activity in DMF

Following transformation, the cells of Example III were plated onto agar plates containing modified Schaeffer's medium [see Leighton and Doi, J. Biol. Chem. 246:3189-3195 (1971)] containing 1% casein. Subtilisin enzyme is secreted by the *B. subtilis*, and active enzyme creates a visible halo surrounding the bacterial colony when it hydrolyzes casein. When the expression of the subtilisin reached a maximal level (determined by the size of the halo), the bacterial clones were transferred, using filter paper, to a second set of agar plates containing 27.5% dimethylformamide (DMF) and 1% casein (referred to herein as "DMf screening plates"). A clone expressing wild-type subtilisin E and a clone expressing a variant known to be more active in DMF (N218S) were also plated as controls. These plates were incubated at 37° C. for 12 to 20 h. Under these conditions a clone expressing wild-type subtilisin E does not produce a detectable halo.

Although the transferred bacteria cannot survive on the DMF screening plates, subtilisin enzyme that is active in the presence of organic solvent could still produce a halo on the screening plates. For those clones which exhibited a halo on the DMF screening plates, the corresponding clones on the original, DMF-free plates were marked for further study. Each marked clone was then selected from the original plates and transferred (using nitrocellulose filters) to a new series of plates containing different DMF concentrations, ranging from 27.5 up to 35%. Those clones showing halos larger than wild-type and N218S mutant clones were subjected to further kinetic analysis and to DNA sequencing.

Cells from these positive clones were grown in 2 ml modified Schaeffer's medium at 37° C. for 16 hours to 20 hours. A small volume of supernatant from each liquid culture was used to assay subtilisin activity in aqueous buffer (10 mM Tris-HCl, pH 8.0 and 10 mM $CaCl_2$), with and without 10% DMF. The activity of the enzyme towards hydrolysis of the specific peptide substrate:

succinyl-Ala-Ala-Pro-Phe-p-nitroanilide was measured as described in Example XI, and the resulting activity compared to the activity of wild-type subtilisin E.

The single mutations Q103R and D97G were identified and isolated by this screening method, starting from DNA encoding wild-type subtilisin E. For random mutagenesis by PCR, and screening of the resulting product, one can also start with a DNA template that contains one or more mutations already found to enhance the activity and/or stability of the enzyme in organic solvents. For example, the double mutant, Q103R+D60N, was discovered by random mutagenesis, starting with DNA encoding the mutant Q103R, and screening the resultant clones as described in Examples II, III and IV.

EXAMPLE V

Screening transformed *B. subtilis* for enhanced subtilisin E stability in DMF

Following transformation, the cells are plated on agar plates of modified Schaeffer's medium containing 1% casein, as described in Example IV. When the expression of the subtilisin reaches a maximum level (determined by the size of the halo), the bacterial clones are transferred, using nitrocellulose paper, to a second set of agar plates containing a set percentage of dimethylformamide (DMF) and 1% casein. These DMF-containing plates are incubated at a specified temperature for a period of time sufficient for deactivation of wild-type (or another control) subtilisin. The enzymes can then be transferred to another set of 1% casein plates (containing no organic solvent) to screen for those that exhibit residual activity. Enzyme that retains activity longer in the presence of the organic solvent can still produce a halo on these screening plates. Those clones which exhibit a halo on the screening plates are putative interesting mutants, and the corresponding clones on the original, DMF-free plates are marked for further stability analysis and DNA sequencing.

EXAMPLE VI

Accumulation of beneficial mutations by sequential random mutagenesis

The subtilisin gene coding for enzyme with four amino acid substitutions D60N+D97G+Q103R+N218S was used as the template for further rounds of random mutagenesis and screening. For each subsequent round of mutagenesis and screening, the target DNA fragments were chosen from the clones identified as positive in the previous round, so that beneficial mutations could be accumulated in the gene. The PCR conditions were modified with respect to those described in Example II by increasing the concentration of dimethylsulfoxide 1.5 times and reducing the concentration of dATP by a factor of two. Furthermore, 45 reaction cycles were used. Following digestion, ligation and transformation of the PCR-generated subtilisin DNA fragments as described in Examples II and III, the clones were screened on agar plates containing 30% DMF. Positive clones were then grown in 2 mL cultures, and the supernatants were assayed in 40% DMF as described in Example XII. The mutant subtilisin DNA was isolated from one positive clone and used for the next round of random mutagenesis. After three sequential random mutagenesis and screening steps, the DNA coding for the mutant subtilisin D60N+D97G+Q103R+G131D+E156G+N181S+S182G+S188P+N218S+T255A (called PC3) was obtained, starting from the 4M variant (D60N+D97G+Q103R+N218S).

EXAMPLE VII

Sequencing of the mutant subtilisin genes

The insert HindIII-BamHI DNA fragment of a mutant subtilisin gene was subcloned into pUC119 for sequencing. *E. coli* was infected using M13 phage K07 [see Vieria and Messing, Methods Enzymol. 153:3-11 (1987)] for producing single-stranded DNA. Single-stranded DNA was isolated as the sequencing template. Sequencing was carried out using the dideoxynucleotide-chain-termination method [see Sanger et al., Proc. Natl. Acad. Sci. USA 74:5463-5467 (1977)] with T7 DNA polymerase [Tabor and Richardson, Proc. Natl. Acad. Sci. USA 84:4767-4771 (1987)]. A DNA template of wild-type subtilisin was used as the control.

EXAMPLE VIII

Site-directed mutagenesis using PCR

To incorporate different amino acids at a particular position in the subtilisin enzyme, site-directed mutagenesis was performed using a modified PCR technique. In each case, an additional oligonucleotide containing the codon sequence for the desired amino acid substitution was used as a primer for the PCR (mutagenic primer). The primer initiated chain extension at the region between the 5' and 3' PCR primers described in Example II. In the first PCR reaction, the mutagenic primer and the 5' primer were used to generate a DNA fragment containing the new base substitutions. The fragment was separated from the primers and isolated by agarose gel electrophoresis. The purified fragment was then used as the new 5' primer in a second PCR reaction with the 3' primer to generate the desired mutated subtilisin DNA fragment. The following subtilisin variants were constructed using this method:

| | | | |
|---|---|---|---|
| Q103S | Q103K | Q103E | E156G |
| N181S | S182G | S188P | T255A |
| D60N + D97G + Q103R + N218S (4M) | | | |
| D60N + D97I + Q103R + N218S | | | |
| D60N + D97T + Q103R + N218S | | | |
| D60N + D97G + Q103R + E156G + N181S + N218S (6M) | | | |
| D60N + D97G + Q103R + G131D + E156G + N181S + N218S (7M) | | | |

EXAMPLE IX

Construction of double mutant (D60N+N218S) and triple mutant (Q103R+D60N+N218S) subtilisin E derivatives To construct the double mutant, D60N+N218S, and the triple mutant, D60N+Q103R+N218S, the appropriate DNA fragments were obtained from the single mutants by double digestion with HindIII and BamHI, followed by partial digestion with HaeIII (for which there are two cutting sites within the HindIII-BamHI insert DNA (see FIG. 1). The appropriate fragments were purified from an agarose electrophoresis gel and ligated to the pUC119 vector using T4 ligase. The constructions were confirmed by DNA sequencing. The HindIII-BamHI DNA fragments containing the multiple mutations were reinserted into pKWC and transformed into *B. subtilis* DB428 for expression, purification, and characterization of the mutant enzymes.

EXAMPLE X

Expression and purification of subtilisin E mutants

*B. subtilis* harboring the pKWC expression vector were grown in modified Schaeffer's medium for approximately 36 hours at 37° C. The purification of wild-type and variant subtilisins E was carried out according to published protocols [Estell et al., J. Biol. Chem. 260:6518–6521 (1985)]. Subtilisin was recovered from the medium by ammonium sulfate precipitation followed by two acetone precipitation steps (employing 50% and 65% acetone, respectively). Following each precipitation, the protein was dialysed against 10 mM sodium phosphate buffer, pH 6.2. The enzyme was then passed through a CM Sepharose column equilibrated with this dialysis buffer. Subtilisin was eluted with a gradient of 0–0.4M NaCl in 10 mM sodium phosphate buffer, pH 6.2. The resulting enzyme was dialyzed against 10 mM Tris-HCl, pH 8.0 and 2 mM CaCl$_2$.

Protein concentrations were determined using the Bio-Rad protein assay, as described by the supplier. The purities of the variant and wild-type subtilisin E preparations were determined by SDS PAGE [Laemmli, U.K., Nature 227:680–685 (1970)]. A major band with a molecular weight about 27 kD was detected in each protein sample, and the purity was estimated to be greater than 95%.

EXAMPLE XI

Enzyme kinetics of mutant subtilisins

The amidase activities of subtilisin and derivatives thereof were measured on the substrate succinyl-Ala-Ala-Pro-Phe-p-nitroanilide (sAAPF-pna) at 37° C. in 0.1M Tris-HCl, pH 8.0 and 10 mM CaCl$_2$. Assays were initiated by mixing the enzyme, the substrate and the reaction buffer. The amount of released p-nitroaniline was measured spectrophotometrically at 410 nm as a function of time. K$_M$ and k$_{cat}$ values for hydrolysis of sAAPF-pna by the subtilisin variants were obtained by nonlinear regression of the data using the program Enzfitter (Biosoft).

Changes in transition-state stabilization energies ($\Delta\Delta G^*$) for the hydrolysis reaction by the enzyme variants and in the mixed solvents were determined from the specificity constants K$_{cat}$/K$_M$ [Wilkinson, Biochemistry 22:3581–3586 (1983)]:

$$\Delta\Delta G = -RT \ln \frac{(k_{cat}/K_M)_{mutant}}{(k_{cat}/K_M)_{wild-type}}$$

Kinetic constants are reported in Table I for the wild-type enzyme and six variants with 3–10 amino acid substitutions.

TABLE I k$_{cat}$, K$_M$, k$_{cat}$/K$_M$ and free energies of transition state stabilization ($\Delta\Delta G^*$) for the hydrolysis of succinyl-Ala—Ala—Pro—Phe-p-nitroanilide by wild-type and variant subtilisin E in 0.1M Tris-HCl, 10 mM CaCl$_2$, pH 8, 37° C.

| Mutant | k$_{cat}$ s$^{-1}$ | K$_M$ (mM) | k$_{cat}$/K$_M$ (M$^{-1}$ s$^{-1}$ × 10$^3$) | $\Delta\Delta G^*$ (kcal mol$^{-1}$) |
|---|---|---|---|---|
| WT | 21 | 0.56 | 38 | — |
| 3M | 40 | 0.11 | 360 | −1.39 |
| 4M | 43 | 0.17 | 249 | −1.17 |
| 6M | 12 | 0.04 | 268 | −1.2 |
| 7M | 18 | 0.03 | 606 | −1.7 |
| PC1 | 16 | 0.05 | 334 | −1.35 |
| PC3 | 27 | 0.10 | 274 | −1.22 |

Legend:
WT = wild-type
3M = D60N + Q103R + N218S
4M = D60N + Q103R + N218S + D97G
6M = D60N + Q103R + N218S + D97G + E156G + N181S
7M = D60N + Q103R + N218S + D97G + E156G + N181S + G131D
PC1 = D60N + Q103R + N218S + D97G + E156G + N181S + S182G + S188P
PC3 = D60N + Q103R + N218S + D97G + E156G + N181S + G131D + S182G + S188P + T255A Values of the k$_{cat}$/K$_M$ ratio for each of the subtilisin mutants are higher than that of the wild-type enzyme. $\Delta\Delta G^*$ values are calculated from the ratio of the catalytic efficiencies of the mutant and wild-type enzymes (as set forth above) and reflect the extent to which the amino acid substitution is effective in enhancing activity. A large negative $\Delta\Delta G^*$ indicates that the mutation preferentially stabilizes the transition state for the reaction and thereby improves the catalytic efficiency of the enzyme.

This example shows that the subtilisin variants are more active than wild-type subtilisin E in aqueous media. Example XII demonstrates that they are also more active in the presence of an organic solvent (DMF).

EXAMPLE XII

Mutant subtilisins with improved amidase activity in the presence of DMF

For activity measurements in mixed buffer (containing DMF), a portion of the aqueous buffer was replaced by the percentage (w/v) of DMF indicated in Table II. Kinetic constants are reported in Table II for the wild-type enzyme and six variants with 3-10 amino acid substitutions in 20% and 40% DMF.

TABLE II $k_{cat}$, $K_M$, $k_{cat}/K_M$ and free energies of transition state stabilization ($\Delta\Delta G^*$) for the hydrolysis of succinyl-Ala—Ala—Pro—Phe-p-nitroanilide by wild-type and variant subtilisin E in 0.1M Tris-HCl, 10 mM $CaCl_2$, pH 8, containing 20% and 40% DMF, 37° C.

| | 20% DMF | | | | 40% DMF | | | |
|---|---|---|---|---|---|---|---|---|
| | $k_{cat}$ $(s^{-1})$ | $K_M$ (mM) | $k_{cat}/K_M$ $(M^{-1}s^{-1} \times 10^{-3})$ | $\Delta\Delta G^*$ (kcal mol$^{-1}$) | $k_{cat}$ $(s^{-1})$ | $K_M$ (mM) | $k_{cat}/K_M$ $(M^{-1}s^{-1} \times 10^{-3})$ | $\Delta\Delta G^*$ (kcal mol$^{-1}$) |
| WT | 17 | 12.2 | 1.4 | — | 3.3 | 20.9 | 0.16 | — |
| 3M | 63 | 1.4 | 44 | −2.15 | 19.9 | 2.94 | 6.8 | −2.32 |
| 4M | 76 | 2.4 | 31.5 | −1.84 | 41.3 | 5.54 | 7.5 | −2.38 |
| 6M | 29 | 1.0 | 28 | −1.85 | 11 | 2.3 | 4.8 | −2.1 |
| 7M | 64 | 0.97 | 66 | −2.37 | 31 | 2.5 | 12.5 | −2.69 |
| PC1 | 20 | 0.3 | 59.7 | −2.33 | 10 | 0.99 | 10.5 | −2.59 |
| PC3 | 73 | 0.7 | 98.9 | −2.63 | 62 | 2.96 | 20.9 | −3.0 |

Legend:
WT = wild-type
3M = D60N + Q103R + N218S
4M = D60N + Q103R + N218S + D97G
6M = D60N + Q103R + N218S + D97G + E156G + N181S
7M = D60N + Q103R + N218S + D97G + E156G + N181S + G131D
PC1 = D60N + Q103R + N218S + D97G + E156G + N181S S182G + S188P
PC3 = D60N + Q103R + N218S + D97G + E156G + N181S + G131D + S182G + S188P + T255A For each set of mutations, the improvement in catalytic efficiency is greater (more negative $\Delta\Delta G^*$) in the presence of DMF than it is in the purely aqueous medium (see Example XI, Table I). The mutations are more effective in improving enzyme amidase activity in 40% DMF than in 20% or purely aqueous buffer.

The activities of several of the variants towards a different peptide substrate, succinyl-Ala-Ala-Pro-Met-p-nitroanilide, were measured in concentrations of DMF as high as 85%. Values of $k_{cat}/K_M$ are plotted in FIG. 2 for wild-type enzyme and two variants, 3M and PC3. All four combination variants 3M, 4M, 7M and PC3, are more active than the wild-type enzyme over a wide range of DMF concentrations.

Figure 2:
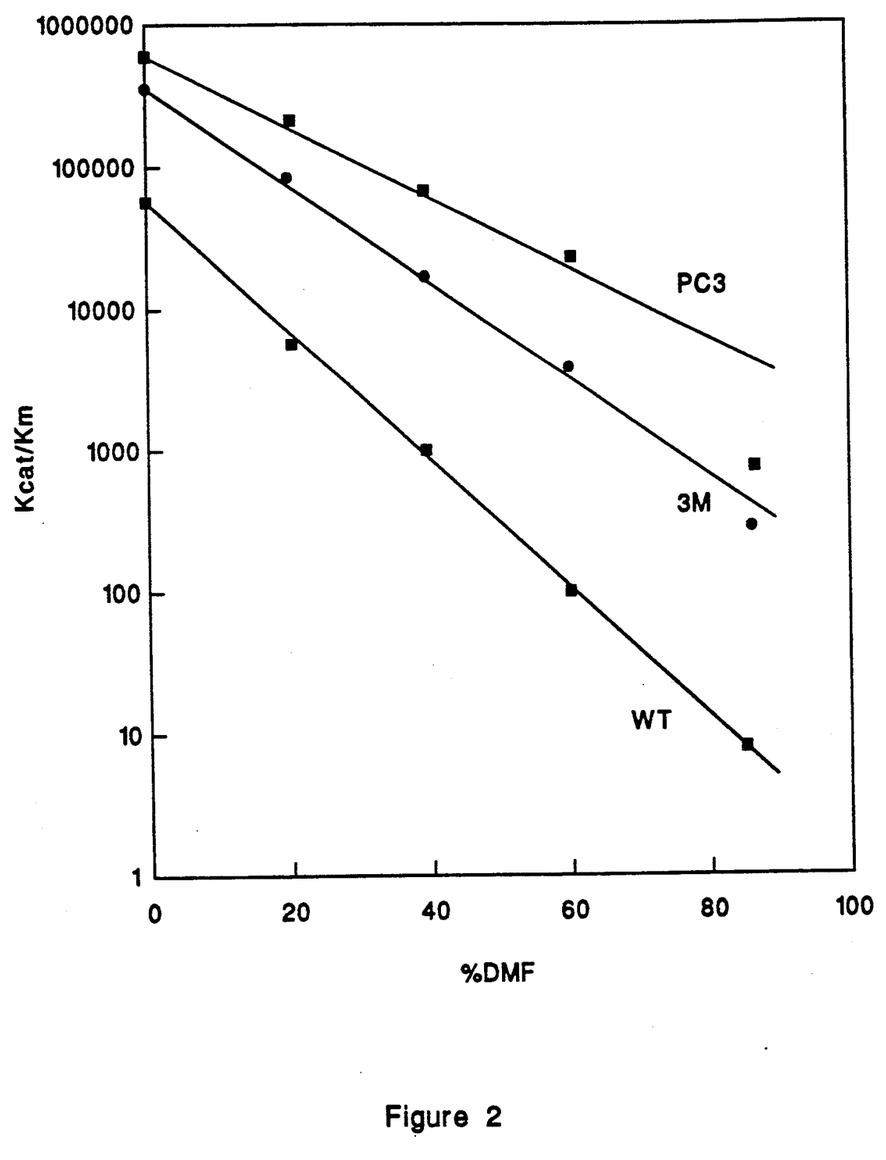
FIG. 2 shows the catalytic efficiency ($k_{cat}/K_M$) for hydrolysis of suc-Ala-Ala-Pro-Met-p-nitroanilide (sAAPM-pna) by wild-type subtilisin E (□), triple subtilisin mutant 3M (Q103R+D60N+N218S; O) and multiple subtilisin mutant PC3 (D60N+Q103R+N218S+D97G+E156G+N181S+G131D+S182G+S188P+T255A; ■).
Figure 3:
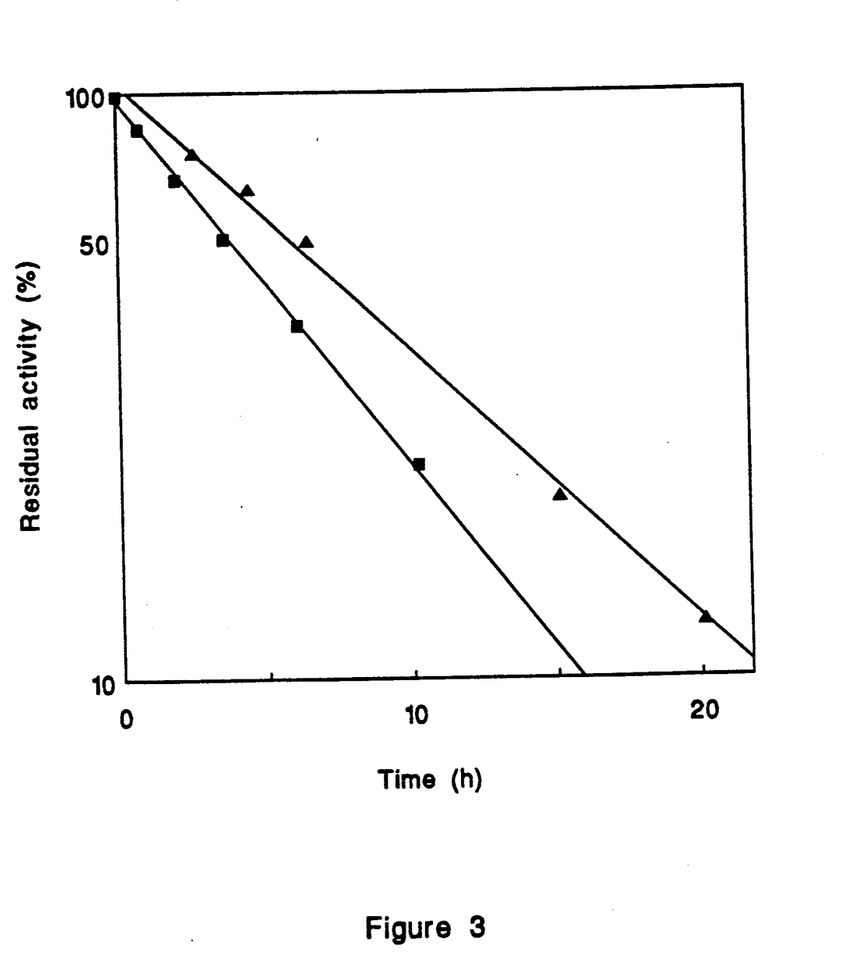
FIG. 3 shows deactivation of wild-type (■) and Q103R+D60N+N218S (▲) subtilisin E in 40% aqueous DMF at 50° C.

These results show that the improvements in catalytic efficiency brought about by the amino acid substitutions are effective over a wide range of solvent conditions, from no organic solvent to 85% DMF. The greatest improvements in catalytic efficiency are observed in high concentrations of organic solvent (>60% DMF). This example also shows that the mutations can also improve activity towards a substrate other than the one used during the screening process.

EXAMPLE XIII

Effects of mutations at position 103 on subtilisin amidase activity and substrate specificity The effects of different amino acid substitutions at position 103 on amidase activity were investigated. The variants Q103E, Q103K, and Q103S were constructed by PCR site-directed mutagenesis as described in Example VIII. The amidase activities of these variants and the variant Q103R identified by random mutagenesis and screening for enhanced activity in the presence of DMF (Example IV) are compared in Table III. The reactions were carried out in 10% DMF according to the procedures outlined in Examples XI and XII.

TABLE III $K_M$, $k_{cat}$, $K_{cat}/K_M$ and free energies of transition state stabilization ($\Delta\Delta G^*$) for the hydrolysis of succinyl-Ala—Ala—Pro—Phe-p-nitroanilide by wild-type and variant subtilisin E in 0.1M Tris-HCl, 10 mM $CaCl_2$, pH 8, with 10% DMF, 37° C.

| Variant | $K_M$ (mM) | $k_{cat}$ $(s^{-1})$ | $k_{cat}/K_M$ $(M^{-1}s^{-1} \times 10^3)$ | $\Delta\Delta G^*$ (kcal mol$^{-1}$) |
|---|---|---|---|---|
| Wild-type | 2.9 | 20 | 7.0 | — |
| Q103R | 1.3 | 34 | 26 | −0.81 |
| Q103S | 3.0 | 20 | 7.0 | 0.0 |
| Q103K | 2.4 | 13 | 5.0 | +0.21 |
| Q103E | 7.1 | 16 | 2.3 | +0.70 |

The Q103R substitution results in the highest activity. This example shows that the random mutagenesis and screening procedure identified an amino acid substitution that is more effective than other amino acid substitutions at the same position.

EXAMPLE XIV

Q103R mutation affects substrate binding/specificity and reflects the substrate used during screening The effects of the Q103R amino acid substitution on amidase activity were investigated for two substrates, succinyl-Ala-Ala-Pro-Phe-p-nitroanilide (negatively-charged succinyl group at the peptide N-terminus) and Ala-Ala-Pro-Phe-p-nitroanilide (positively charged N-terminus) in 10% DMF. Kinetics parameters are reported in Table IV.

TABLE IV $k_{cat}$, $K_M$, $k_{cat}/K_M$ and free energies of transition state stabilization ($\Delta\Delta G^*$) for the hydrolysis of succinyl-Ala—Ala—Pro—Phe-p-nitroanilide by wild-type subtilisin E and Q103R variant thereof in 0.1M Tris-HCl, 10 mM $CaCl_2$, pH 8, with 10% DMF, 37° C.

| | $K_M$ (mM) | $k_{cat}$ $(s^{-1})$ | $k_{cat}/K_M$ $(M^{-1}s^{-1} \times 10^3)$ | $\Delta\Delta G^*$ (kcal mol$^{-1}$) |
|---|---|---|---|---|
| Suc-AAPFpna | | | | |
| WT | 0.51 | 21 | 41 | — |
| Q103R | 0.27 | 34 | 126 | −0.69 |
| AAPFpna | | | | |

TABLE IV-continued $k_{cat}$, $K_M$, $k_{cat}/K_M$ and free energies of transition state stabilization ($\Delta\Delta G^*$) for the hydrolysis of succinyl-Ala—Ala—Pro—Phe-p-nitroanilide by wild-type subtilisin E and Q103R variant thereof in 0.1M Tris-HCl, 10 mM CaCl$_2$, pH 8, with 10% DMF, 37° C.

|  | $K_M$ (mM) | $k_{cat}$ (s$^{-1}$) | $k_{cat}/K_M$ (M$^{-1}$s$^{-1}$ × 10$^3$) | $\Delta\Delta G^*$ (kcal mol$^{-1}$) |
|---|---|---|---|---|
| WT | 7.8 | 0.83 | 0.11 | — |
| Q103R | ≧37 | ≧2.6 | 0.07 | +0.25 |

The Q103R mutation decreases $K_M$ for the negatively charged peptide substrate (suc-AAPFpna), but dramatically increases $K_M$ for the positively charged substrate. Succinyl-Ala-Ala-Pro-Phe-p-nitroanilide was used during the final screening step for this mutant. This example demonstrates that the effectiveness and substrate specificity of the random mutations that are found can strongly depend on the substrate used during the screening process.

EXAMPLE XV

Effects of individual mutations on amidase activity of subtilisins in the presence and absence of DMF Kinetic constants are presented in Table V for the hydrolysis of Succinyl-Ala-Ala-Pro-Phe-p-nitroanilide by variants containing the nine individual amino acid substitutions found by the random mutagenesis and screening procedures outlined in Examples II, III, IV and V and a double variant containing the D60N+N218S substitutions.

demonstrates the utility of accumulating mutations using the method outlined in Example VI.

EXAMPLE XVI

The effects of mutations can be additive

To some extent mutations identified in separate mutagenesis and screening experiments can be combined to obtain cumulative improvements in enzyme activity. The additivity of mutations can be ascertained by comparing the $\Delta\Delta G^*$ values for the single variant (see Example XV, Table V) with those of combination variants (see Example XII, Table II). For example, the triple variant D60N+Q103R+N218S has $\Delta\Delta G^*$ of −2.15 with respect to wild type in 20% DMF (3M, Table V). The individual mutations are −0.51 (−0.98) +(−0.61)=−2.1, which is almost identical to the $\Delta\Delta G^*$ observed in the variant containing all three mutations. Thus the effects of these three mutations are additive.

Additivity is not observed, however, for all mutations under all conditions. For example, the mutation D97G alone increases catalytic efficiency $k_{cat}/K_M$ by more than two-fold in 20% DMF (Table IV) ($\Delta\Delta G^* = -0.64$ kcal/mol). However, when this mutation is combined with D60N+Q103R+N218S to make 4M, the incremental change in $\Delta\Delta G^*$ is not −0.64, but rather +0.3 (Table II, 4M versus 3M in 20% DMF). In this case, the effect of the mutation on 3M is to decrease its activity, the opposite to what was observed for the effect of the single mutation. In 40% DMF, however,

TABLE V $k_{cat}$ $K_M$, $k_{cat}/K_M$ and free energies of transition state stabilization ($\Delta\Delta G^*$) for the hydrolysis of succinyl-Ala—Ala—Pro—Phe-p-nitroanilide by wild-type subtilisin E and variants thereof in 0.1M Tris-HCl, 10 mM CaCl$_2$, pH 8, containing 0% and 20% DMF, 37° C.

| | 0% DMF | | | | 20% DMF | | | |
|---|---|---|---|---|---|---|---|---|
| | $k_{cat}$ (s$^{-1}$) | $K_M$ (mM) | $k_{cat}/K_M$ (M$^{-1}$s$^{-1}$ × 10$^{-3}$) | $\Delta\Delta G^*$ (kcal mol$^{-1}$) | $k_{cat}$ (s$^{-1}$) | $K_M$ (mM) | $k_{cat}/K_M$ (M$^{-1}$s$^{-1}$ × 10$^{-3}$) | $\Delta\Delta G^*$ (kcal mol$^{-1}$) |
| WT | 21 | 0.56 | 38 | — | 17 | 12.2 | 1.4 | — |
| D60N | 22 | 0.53 | 42 | −0.06 | 23 | 7.6 | 3.1 | −0.51 |
| D97G | 20 | 0.27 | 74 | −0.41 | 21 | 5.2 | 4 | −0.64 |
| Q103R | 31 | 0.25 | 124 | −0.73 | 18 | 2.7 | 6.8 | −0.98 |
| G131D | 39 | 1.15 | 33 | +0.09 | 29 | 10.6 | 2.8 | −0.43 |
| E156G | 10 | 0.25 | 39 | −0.02 | 12 | 7.8 | 1.5 | −0.04 |
| N181S | 27 | 0.23 | 120 | −0.71 | 17 | 3.8 | 4.4 | −0.71 |
| S182G | 18 | 0.47 | 38 | 0.0 | 11 | 8.0 | 1.4 | 0.0 |
| S181P | 19 | 0.52 | 37 | +0.02 | 10 | 6.1 | 1.6 | −0.08 |
| N218S | 36 | 0.45 | 81 | −0.46 | | | 3.9 | −0.61 |
| T255A | 7 | 0.14 | 52 | −0.19 | 6 | 3.0 | 1.8 | −0.17 |

Several of the mutations (D60N, E156G, S188P, S182G) have little effect by themselves on the amidase activity of the enzyme in water. The substitution G131D in fact decreases the enzyme activity in water. In contrast, some of those mutations significantly enhance activity in 20% DMF. For example, D60N is only 10% more efficient than wild-type in water ($\Delta\Delta G^* = -0.06$ kcal/mol), but is 200% better in 20% DMF ($\Delta\Delta G^* = -0.51$ kcal/mol). This demonstrates the utility of screening in the presence of the organic solvent in order to identify amino acid substitutions effective for improving catalytic activity in organic media.

Several of the mutations by themselves still have little effect on the amidase activity in 20% DMF (S182G, S188P, E156G). Nonetheless, when combined with other mutations in the variants 6M, 7M, PC1 and PC3, these mutations have a beneficial affect on activity. This the effect of D97G is to slightly increase the catalytic efficiency of 3M. This demonstrates that individual mutations can be combined with beneficial cumulative improvements in catalytic activity under some conditions.

EXAMPLE XVII

Location of mutations relative to the active site and/or substrate binding pocket The locations of the various mutations found to increase subtilisin E activity in the presence of DMF were found within the subtilisin E three-dimensional structure. Four of the mutations were found to be in the substrate binding pocket: D97G, Q103R, E156G and N218S. Other mutations were found to be close to the catalytic triad in the enzyme active site: D60N and E156G. The mutations are all clustered in a region that encompasses the active site and substrate binding pocket.

Using the PCR technique described in Examples II and VI, mutations were introduced randomly throughout the subtilisin E gene fragment that was targeted. However, the screening process identified only mutations that were clustered in a particular region of the protein. This demonstrates that all, or a majority of, mutations that enhance catalytic activity in the organic solvent are located in or near the active site or substrate binding pocket.

EXAMPLE XVIII

Location of mutations relative to subtilisin variable regions

Figure 4:
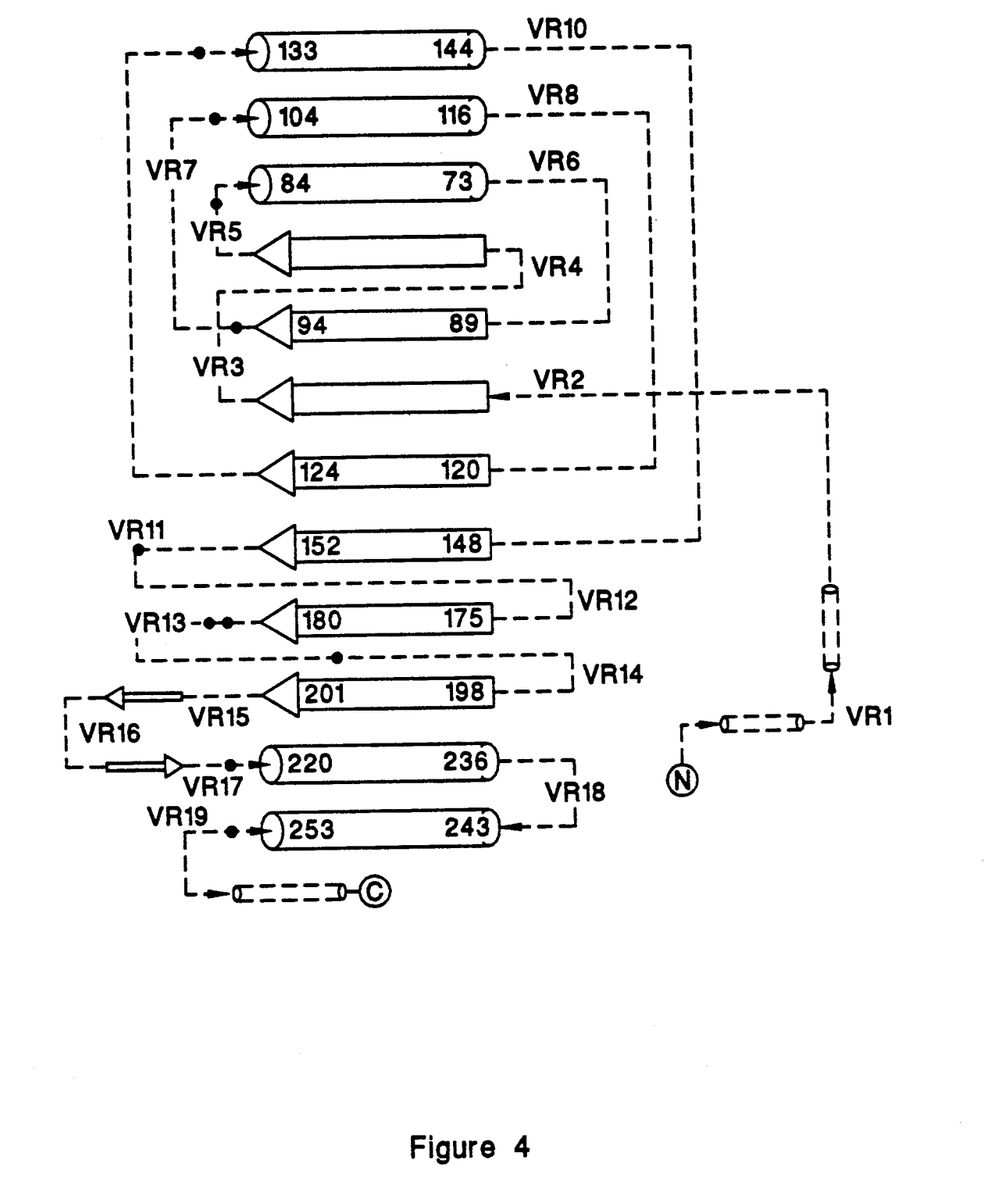
FIG. 4 shows the secondary structural topology of subtilisins. α-helices are shown as cylinders, B-sheet strands as arrows. Solid lines indicate regions of conserved amino acids (SCRs), dashed lines indicate variable regions (VRs). Locations of amino acid substitutions listed in Table V are indicated by ●.

Dijkstra and coworkers have compared the amino acid sequences of more than 40 subtilisins from different sources [see Siezen et al., supra]. FIG. 4 shows a schematic representation of the secondary structure topology of the subtilisins, indicating those regions of the sequence that are conserved (SCRs) and those that are not conserved (i.e., variable regions, or VRs). Other amino acids are commonly found in the variable regions of the sequences of other natural subtilisins. The locations of the 10 amino acid substitutions listed in Table V are also marked on FIG. 4. Nine out of these ten substitutions are found either in variable regions, or in close proximity to the variable regions.

These observations demonstrate that amino acid substitutions likely to give beneficial effects on enzyme activity will be located in, or near, the variable regions of the protein amino acid sequence. The variable regions can be determined by sequence comparisons with homologous enzymes.

EXAMPLE XIX

Mutant subtilisins exhibit improved esterase activity in the presence of DMF

The esterase activities of the wild-type and mutant subtilisins were investigated for hydrolysis of the peptide ester substrate succinyl-Ala-Ala-Pro-Phe-thiobenzyl ester in the presence of 70% DMF. The reactions were carried out in 1.5 mL of 70% DMF, with 150 μL of 0.1M Tris-HCl, pH 8.2, 0.1M NaCl buffer and 5 μL dithiodipyridine (0.16M in DMF) at 37° C. Assays were initiated by mixing the enzyme, substrate and reaction buffer. The activity was measured spectrophotometrically at 324 nm. $K_M$ and $k_{cat}$ values were obtained by nonlinear regression using the program Enzfitter (Biosoft). Kinetic constants are reported in Table VI for wild-type subtilisin E and two mutants with 3 and 10 amino acid substitutions.

TABLE VI $k_{cat}$, $K_M$, $k_{cat}/K_M$ for the hydrolysis of succinyl-Ala—Ala—Pro—Phe-thiobenzyl ester by wild-type subtilisin E and mutants thereof in 70% DMF, 37° C.

| Mutant | $k_{cat}$ s$^{-1}$) | $K_M$ (mM) | $k_{cat}/K_M$ (M$^{-1}$ s$^{-1}$ × 10$^3$) |
|---|---|---|---|
| WT | 80 | 59 | 1.4 |
| 3M | 222 | 25 | 8.9 |
| PC3 | 292 | 18 | 16 |

Legend:
WT = wild-type
3M = D60N + Q103R + N218S
PC3 = D60N + Q103R + N218S + D97G + E156G + N181S + G131D + S182G + S188P + T255A Both triple mutant 3M and the mutant containing 10 amino acid substitutions (PC3) are more active in ester hydrolysis than the wild-type enzyme. This example demonstrates that the mutant subtilisins also exhibit improved esterase activity in the presence of a high concentration of polar organic solvent.

EXAMPLE XX

Transesterification of N-acetyl-L-phenylalanine methyl ester in different organic solvents The activity of the D60N+Q103R+N218S (3M) subtilisin E triple variant was compared to that of the wild-type enzyme for the transesterification of N-acetyl-L-phenylalanine methyl ester to the ethyl ester in three organic solvents. The reactions were carried out in 2 mL volumes of the indicated solvent, containing 1 mg/mL of enzyme, 100 mM N-acetyl-L-phenylalanine methyl ester, 1M ethanol. The samples were incubated, with shaking, at 32° C., and the formation of the ethyl ester product was measured by capillary gas chromatography. Values of the kinetic constants $k_{cat}/K_M$ are given in Table VII for the wild-type and 3M variant enzymes. In all three solvents, anhydrous hexane, hexane containing 0.1% water, and acetonitrile containing 0.1% water, the D60N+Q103R+N218S (3M) triple variant was considerably more efficient than the wild-type enzyme.

TABLE VII $k_{cat}/K_M$ for transesterification of N-acetyl-L-phenylalanine methyl ester by subtilisin E (wild-type and variant 3M (D60N + Q103R + N218S) in three different organic solvents, at 32° C.

| Solvent | $k_{cat}/K_M$ (Min$^{-1}$ mg$^{-1}$ × 10$^{-3}$) WT | 3M | $\frac{(k_{cat}/K_M)3M}{(k_{cat}/K_M)WT}$ |
|---|---|---|---|
| hexane (anhydrous) | 0.4 | 17 | 43 |
| hexane (0.1% water) | 5 | 220 | 43 |
| CH$_3$CN (0.1% water) | 0.3 | 3.1 | 10 |

This example demonstrates that the mutant subtilisins can exhibit enhanced activity in a transesterification reaction. Furthermore, the enhanced activity is observed in organic solvents other than DMF. Finally, enhanced activity is observed in an anhydrous solvent.

EXAMPLE XXI

Improved peptide synthesis using mutant subtilisins

The synthesis of peptide polymers by the mutant subtilisins was investigated in DMF using methionine methyl ester as the substrate. Approximately 250 μg subtilisin E variant 3M (D60N+Q103R+N218S) was added to a 1 mL reaction solution containing 60% or 70% (v/v) DMF, 0.75 μL triethylamine, and 150 mg of methionine methyl ester hydrochloride. The reaction was carried out at room temperature for 24 to 48 hours with constant rotation of the tube. The precipitated polymer was collected by centrifugation, washed several times with water and dried.

The polymer was then subjected to amino acid analysis. A portion of the polymer was hydrolyzed with acid at high temperature, and the content of free amino acid in the hydrolyzed sample was compared to that in the unhydrolyzed polymer. A peak corresponding to free methionine appeared only in the assay on the hydrolyzed polymer, indicating that the precipitated material was a polymer of methionine, i.e., poly(methionine). Mass spectrometric analysis of the polymer synthesized by 3M subtilisin in 70% DMF showed a molecular weight of approximately 4700 and a degree of polymerization of approximately 36. Wild-type subtilisin E synthesized no detectable polymer at this concentration of DMF (70%). In 60% DMF, wild-type subtilisin catalyzed the polymerization of methionine to yield a product with a molecular weight of 1000-1500 and a degree of polymerization of approximately 10.

This example shows that the mutant subtilisin 3M is effective in peptide synthesis in organic solvents. The mutant enzyme can produce poly(methionine) in a high concentration of organic solvent (70% DMF), where the wild-type enzyme is inactive. Furthermore, a higher degree of polymerization (a longer polymer) is achieved using the mutant enzyme in 70% DMF than using wild-type enzyme in 60% DMF.

EXAMPLE XXII

Stability of mutant subtilisins

Stabilities of the various mutant subtilisins were determined from the loss of activity as a function of time at a fixed temperature. The enzymes were incubated at 25° C. in 10 mM Tris-HCl, pH 8.0, 2 mM CaCl$_2$ with 70% (v/v) DMF. The residual amidase activities were measured by diluting not more than 100 μL of the enzyme solution into a standard 1.5 mL reaction mixture for the amidase activity assays described in Example XI. The residual activities are reported in Table VIII.

TABLE VIII

| Residual amidase activities of wild-type and mutants of subtilisin E in 70% DMF, 25° C. | | | |
|---|---|---|---|
| Mutant | 60 h | 130 h | 460 h |
| WT | 88% | 85% | 49% |
| 3M | 98% | 96% | 63% |
| 7M | 94% | 91% | 55% |
| PC3 | 91% | 85% | 41% |

Legend:
WT = wild-type
3M = D60N + Q103R + N218S
7M = D60N + Q103R + N218S + D97G + E156G + N181S + G131D
DC3 = D60N + Q103R + N218S + D97G + E156G + N181S + G131D + S182G + S188P + T255A The 3M and 7M mutant subtilisins appear to be more stable than wild-type in 70% DMF at 25° C. All the variants are stable for a period of many days in 70% DMF. This example demonstrates that the amino acid substitutions can enhance activity without compromising the stability of the enzyme.

EXAMPLE XXIII

Subtilisins exhibiting enhanced stability in organic solvents

Site-directed mutagenesis

The following four deoxyoligonucleotides, corresponding to the specific mutations Asp248→Asn, Ala or Leu (D248N, D248A, or D248L); and Asn 218→Ser (N218S) were used for site-directed mutagenesis of the HindIII-BamHI DNA fragment of 789 basepairs, covering the amino acid sequence from Ser 49 to the C-terminus of the mature subtilisin E gene, according to the in vitro site-directed mutagenesis kit from Amersham:

SEQ ID NO. 4:
5'-TTTCTAAACG<u>GTT</u>ACGGACTTGC-3',

SEQ ID NO. 5: 5'-CTAAACG<u>AGC</u>ACGGACT-3',

SEQ ID NO. 6: 5'-CTAAACG<u>AAG</u>ACGGACT-3', and

-continued
SEQ ID NO. 7: 5'-CGCTTAT<u>AGC</u>GGAACGT-3'.

Mutants in *E. coli* TG1 were screened by DNA sequencing according to the T7 Sequencing™ Kit from Pharmacia LKB. The unique HindIII-NcoI fragment of the D248N subtilisin E gene was replaced by the corresponding fragment of the N218S gene to obtain the double mutant N218S+D248N. All variants were sequenced a second time to confirm the mutations. Plasmid pKWC was used for expression of subtilisin E in *Bacillus subtilis* DB428, which does not produce additional extracellular proteases.

Stability measurement

To determine the kinetic stabilities, lyophilized enzymes (from 2 mM CaCl$_2$, 10 mM Tris, pH=8) were redissolved in the same volume of solvent mixture (80% (v/v) DMF, 20% H$_2$O or 40% DMF, 60% H$_2$O) and incubated at 30° C. or 50° C. Because the stability of subtilisin strongly depends on the calcium ion concentration, it was necessary to maintain a constant CaCl$_2$ concentration in the DMF/water incubation mixture. Enzyme concentrations were mM or less. The samples were prepared so that all the variants showed similar initial activities, and residual hydrolytic activities were measured on sAAPF-pna at 37° C. in 0.1M Tris-HCl, 10 mM CaCl$_2$, pH 8.0, as described in Example XI after incubation in the organic solvent. Half-lives for the various mutant subtilisins are reported in Table IX.

TABLE IX

| Half-lives for inactivation of wild-type and variants of subtilisin E in the presence of DMF. | | |
|---|---|---|
| Variant | 80% DMF, 30° C. t$_½$ (h) | 40% DMF, 50° C. t$_½$ (h) |
| WT | 5.7 | 4.7 |
| D248N | 10.2 | 3.7 |
| D248A | 10.3 | 3.6 |
| D248L | 11.1 | 4.2 |
| N218S | 10.2 | 10.0 |
| N218S + D248N | 19.2 | 8.0 |

Each of the variants is significantly more stable than the wild-type enzyme in the presence of DMF. The double variant N218S+D248N is more than three times as stable as the wild-type enzyme in 80% DMF. This example also demonstrates that mutations affecting subtilisin stability in organic solvents can be combined to obtain greater enhancements.

While the invention has been described in detail with reference to certain preferred embodiments thereof, it will be understood that modifications and variations are within the spirit and scope of that which is described and claimed.

Summary of Sequences

Sequence ID No. 1 is the amino acid sequence of wild-type subtilisin E.

Sequence ID Nos. 2 and 3 are PCR primer sequences used for the random mutagenesis of subtilisin E.

Sequence ID Nos. 4-6 are deoxyoligonucleotides, corresponding to the specific mutations D248N, D248A, D248L, and N218S, respectively. These oligos were used for site-directed mutagenesis of the HindIII-BamHI DNA fragment of the mature subtilisin E gene.

That which is claimed is:

1. A substantially pure modified subtilisin enzyme having improved stability and/or catalytic activity in organic media, relative to the stability and/or catalytic activity of unmodified subtilisin enzymes in organic media, wherein said modified subtilisin enzyme is selected from among the group consisting of mature, Class I subtilisins and wherein the modification consists of an amino acid substitution at amino acid sequence position 181 of said Class I subtilisin enzyme which corresponds substantially to position 181 of the mature subtilisin BPN', said substitution consisting of N181S.

2. A modified subtilisin enzyme according to claim 1 wherein said Class I subtilisin enzyme is selected from BASBPN, BSS168, BSSDY, BLSCAR, BAPB92, BYSYAB, BLS147, BSEPR, BSISP1, TVTHER, DNEBPR, XCEXPR, BSBPF, EFCYLA, SEEPIP, SPSCPA, LLSK11, SMEXSP, AVPRCA, MMPPC3, HSIPC2, HSFURI, DMFUR1, KLKEX1, or SCKEX2.

3. A modified subtilisin enzyme according to claim 2, wherein said Class I subtilisin enzyme is selected from BASBPN, BSS168, BSSDY, BLSCAR, BAPB92, BYSYAB, BLS147, BSEPR, BSISP1, or TVTHER.

4. An isolated DNA segment consisting essentially of a region encoding the modified enzyme of claim 1.

5. An expression vector containing DNA according to claim 4.

6. Host cells containing DNA according to claim 4.

7. Host cells containing expression vector according to claim 5.

8. Process for the production of modified enzyme according to claim 1, said process comprising expressing DNA encoding said modified enzyme in a suitable host.

9. A modified subtilisin enzyme according to claim 1 wherein said modification consists of one or more additional amino acid substitutions at amino acid sequence positions of said Class I subtilisin enzyme corresponding substantially to those of the amino acid sequence of the mature subtilisin BPN', said substitutions selected from the group consisting of D60N, D97G, Q103R, G131D, S182G, S188P, D248A, D248L, D248N or T255A, and optionally E156G and/or N218S.

10. A modified subtilisin enzyme according to claim 9 wherein said substitution consists of D60N.

11. A modified subtilisin enzyme according to claim 9 wherein said substitution consists of D97G.

12. A modified subtilisin enzyme according to claim 9 wherein said substitution consists of Q103R.

13. A modified subtilisin enzyme according to claim 9 wherein said substitution consists of G131D.

14. A modified subtilisin enzyme according to claim 9 wherein said substitution consists of E156F.

15. A modified subtilisin enzyme according to claim 9 wherein said substitution consists of S182G.

16. A modified subtilisin enzyme according to claim 9 wherein said substitution consists of S188P.

17. A modified subtilisin enzyme according to claim 9 wherein said substitution consists of N218S.

18. A modified subtilisin enzyme according to claim 9 wherein said substitution consists of D248N.

19. A modified subtilisin enzyme according to claim 9 wherein said substitution consists of T255A.

20. A modified subtilisin enzyme according to claim 9 wherein said substitution consists of D60N, Q103R and N218S.

21. A modified subtilisin enzyme according to claim 9 wherein said substitution consists of D60N, D97G, Q103R and N218S.

22. A modified subtilisin enzyme according to claim 9 wherein said substitution consist of D60N, G131D and S188P.

23. A modified subtilisin enzyme according to claim 9 wherein said substitution consists of D97G, Q103R, E156G, and T255A.

24. A modified subtilisin enzyme according to claim 9 wherein said substitution consists of D60N, D97G, Q103R, G131D, E156G, S182G, S188P and N218S.

25. A modified subtilisin enzyme according to claim 9 wherein said substitution consists of D60N, D97G, Q103R, G131D, E156G, S182G, S188P, N218S, D248L and T255A.

* * * * *